United States Patent
Barnes

(10) Patent No.: US 7,635,976 B2
(45) Date of Patent: Dec. 22, 2009

(54) SURVEYING OF BURIED PIPELINES

(75) Inventor: Peter Barnes, Bridgeyate Bristol (GB)

(73) Assignee: Dynalog Electronics Ltd., Bristol (GB)

( * ) Notice: Subject to any disclaimer, the term of this patent is extended or adjusted under 35 U.S.C. 154(b) by 496 days.

(21) Appl. No.: 10/589,061

(22) PCT Filed: Feb. 11, 2005

(86) PCT No.: PCT/GB2005/000470

§ 371 (c)(1), (2), (4) Date: Sep. 7, 2006

(87) PCT Pub. No.: WO2005/080934

PCT Pub. Date: Sep. 1, 2005

(65) Prior Publication Data

US 2007/0126421 A1   Jun. 7, 2007

(30) Foreign Application Priority Data

Feb. 12, 2004   (GB) ................. 0403164.7

(51) Int. Cl.
  *G01N 27/82*  (2006.01)
  *G01N 27/72*  (2006.01)
  *G01R 35/00*  (2006.01)
(52) U.S. Cl. ................. 324/240; 324/202; 324/228
(58) Field of Classification Search ............. 324/228, 324/234, 238–240, 242–243, 202; 73/38
See application file for complete search history.

(56) References Cited

U.S. PATENT DOCUMENTS

| 4,390,836 A | 6/1983 | Bruce et al. ............ 324/54 |
| 4,672,321 A | 6/1987 | Howell |
| 5,126,654 A | 6/1992 | Murphy et al. ........ 324/71.2 |
| 5,785,842 A | 7/1998 | Speck ................ 205/777.5 |
| 6,194,902 B1 | 2/2001 | Kuo et al. ............ 324/637 |

FOREIGN PATENT DOCUMENTS

| EP | 0 855 595 A2 | 7/1998 |
| GB | 2 281 398 A | 3/1995 |

OTHER PUBLICATIONS

Proceedings from NACE Conference 1987, "Electromagnetic Techniques for Monitoring Pipeline Coatings", *Corrosion* 87, vol. 311, Mar. 1987, pp. 1-10.

*Primary Examiner*—Bot L LeDynh
(74) *Attorney, Agent, or Firm*—Woodard, Emhardt, Moriarty, McNett & Henry LLP

(57) ABSTRACT

A method of surveying a pipeline is provided. The pipeline comprises a tubular member with a protective wrapping. The method comprises the steps of applying signal to the pipeline from a first location, which first location is remote from the pipeline, and measuring the signal from a second and third locations. The second and third locations are remote from the pipeline and the second location is spaced from the third location along the pipeline. The signals received at the second and third location are used to provide an indication of deterioration of the signal along the tubular member and/or wrapping between the second and third locations.

21 Claims, 8 Drawing Sheets

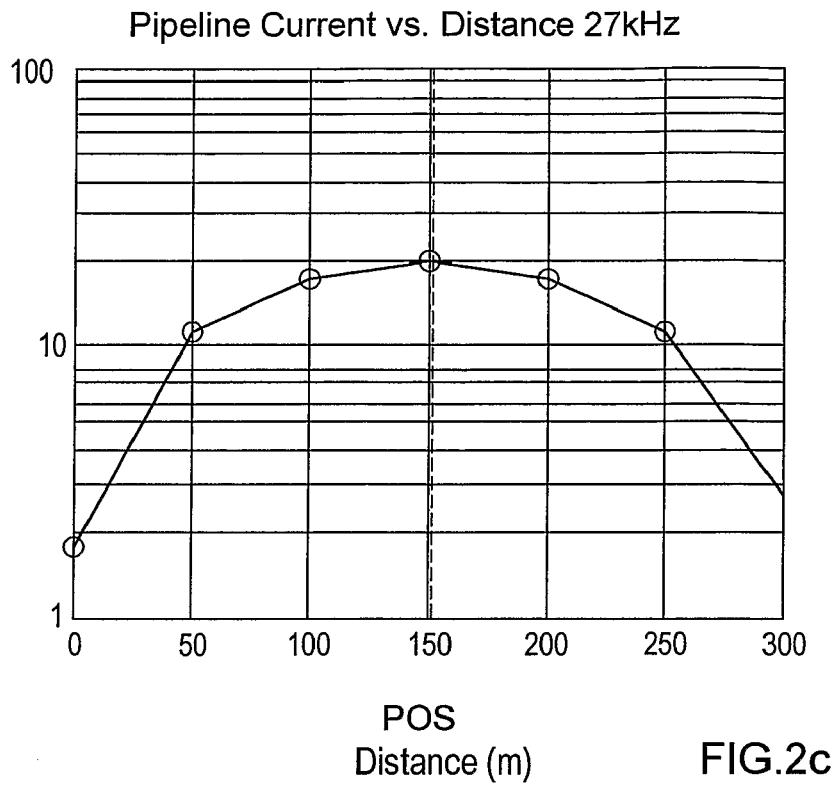
FIG.2c
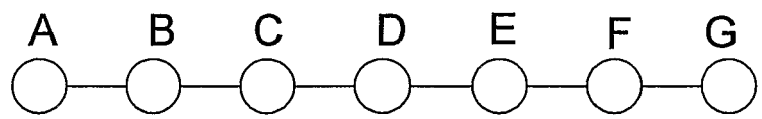
FIG.3
| Emitter | Blank Sections | Measured Sections |
|---|---|---|
| A | AB | BC-CD-DE-EF-FG |
| B | AB-BC | CD-DE-EF-FG |
| C | BC-CD | AB-DE-EF-FG |
| D | CD-DE | AB-BC-EF-FG |
| E | DE-EF | AB-BC-CD-FG |
| F | EF-FG | AB-BC-CD-DE |
| G | FG | AB-BC-CD-DE-EF |
FIG.4

SURVEYING OF BURIED PIPELINES

CROSS-REFERENCES TO RELATED APPLICATIONS

This application is a National Stage filing of International Application PCT/GB2005/000470, filed Feb. 11, 2005, entitled "SURVEYING OF BURIED PIPELINES", claiming priority to United Kingdom Application No. 0403164.7, filed Feb. 12, 2004, entitled "PIPELINE SURVEYING". The subject application claims priority to PCT/GB2005/000470 and to United Kingdom Application No. 0403164.7 and both references are expressly incorporated by reference herein, in their entirety.

BACKGROUND OF THE INVENTION

The present invention relates to a method of surveying pipeline and a pipeline survey apparatus for use in a method for surveying a pipeline.

Pipelines are often used for carrying gases or liquids from one place to the other. These pipelines are often provided with a protective wrapping and/or a cathodic protection system to enhance the life of a buried pipeline. However, over time faults may occur in the wrapping leading to damage of the pipeline. Possible causes of these faults are incorrectly applied wrapping, mechanical damage to the wrapping occurring before, during or after installation, decay of the wrapping due to soil conditions or disbonding of the wrap from the pipeline allowing water to reach the pipe.

Damage to or deterioration of the pipeline may be more or less serious depending on the nature of the gas or liquid that the pipeline is carrying and the areas through which the pipeline is carrying it. Of particular concern are those pipelines carrying hazardous fluids through high consequence areas. A high consequence area is defined as an area which contains a high level of permanent population, a transitional population (e.g. a football stadium, a school etc.), substantial property (buildings, museums etc) or unusually sensitive environment locations (wetland, bay areas, protected species habitats etc).

It is desirable to be able to monitor the state of the pipeline/wrapping in high consequence areas.

Also of concern are sections of pipeline which are identified as "could affect" sections of pipelines. These sections of pipeline have potential for causing death, damage, destruction or a combination of these at a location remote from the location of pipeline rupture. A section of pipeline may be a "could affect" section of pipeline due to the local terrain, the presence of ground or subsurface water, nature of local drainage (natural and man made), or the local weather conditions. Whilst a gas pipeline would not normally contain "could affect" sections of pipeline (since in general all the consequences of a leak or rupture would be local to the leak or rupture) an exception would be an LPG (liquefied petroleum gas) pipeline. A leak in an LPG pipeline would produce a vapour cloud which would stay close to the ground. This cloud is likely to flow to the lowest point in the local terrain, which may be several kilometres away.

Again, it is desirable to be able to monitor the pipeline and/or wrapping integrity in "could affect" sections of pipeline. Accordingly it is an object of the present invention to provide a method of surveying a pipeline which allows deterioration of sections of pipeline and/or wrapping to be monitored.

The Applicants currently market C-Scan survey systems for monitoring the location and condition of buried pipeline. In this system a signal generator is attached to a section of pipeline. The signal generator produces a constant AC current which passes down the pipeline, typically over a distance of 2 to 3 km. A hand held detector unit is used to measure electromagnetic signals, which radiate from the pipeline, at a series of locations spaced down the pipeline from the signal generator. The signals detected by the detector unit allow a user to monitor attenuation of the AC current down the pipeline from the signal generator. The rate of decline of the AC current is dependent primarily on the electrical resistivity of the wrap or coating used and the area of the wrapping in contact with the soil per unit length. However, if there is a low resistance electrical path between the pipeline and the soil at any point, a substantial increase in loss of signal current occurs. This increase in loss of signal current may be detected by the hand held detector unit. An increase in loss of signal current may indicate incorrectly applied wrapping, mechanical damage to the wrap, decay of the wrap due to soil conditions, disbanding of the wrap from the pipeline allowing water to penetrate through to the pipeline and or a leak in the pipeline itself.

However, this existing system requires identification of an appropriate point in the pipeline at which the signal generator may be attached. Further, the location of the signal generator may be determined by the points on the pipeline where it is possible to attach the signal generator. Thus a fault located near the signal generator can make it difficult to monitor sections of the pipeline beyond the fault.

It is an object of the present invention to provide an alternative method and apparatus for surveying a pipeline.

According to a first aspect of the present invention there is provided a method of surveying a buried pipeline, which pipeline comprises a tubular member with a protective wrapping, comprising the step of applying a signal to the pipeline from a first location, which first location is remote from the pipeline, and measuring the signal from a second location and a third location, which second and third locations are remote from the pipeline, the second location being spaced from the third location along the pipeline and using the signals received at the second location and third location to provide an indication of deterioration of the tubular member and/or wrapping.

According to a second aspect of the present invention there is provided a method of surveying a buried pipeline, which pipeline comprises a tubular member with a protective wrapping, comprising the step of selecting a plurality of spaced locations above and along the length of the pipeline, and sequentially from each spaced location applying a signal to the pipeline and measuring the signal at each of the other spaced locations.

The signal applied to the pipeline may be an AC electric current generated by electromagnetic induction. The step of applying a signal to the pipeline may comprise the step of using non-contact coupling means to apply a signal to the pipeline. The non-contact coupling means may be an electromagnetic signal transmitter. The advantage in being able to apply a current from a location remote from the pipeline is that it allows more freedom when selecting the point along the pipeline at which a signal is applied. This allows, for example, a signal to be applied from either side of a significant fault in the pipeline in order to determine the state of the pipeline lying either side of the fault.

Through out this specification "protective wrapping" shall be taken to mean any coating or wrapping applied to a tubular member to reduce or prevent damage to the tubular member.

In a method according to the first aspect of the present invention the difference between the strength of the signal measured at the second location and the signal measured at the third location may be representative of attenuation of the signal and along the tubular member and/or wrapping. The method may further comprise the step of comparing the attenuation of the signal along the tubular member and/or wrapping with a predetermined expected attenuation in order to provide an indication of deterioration of the tubular member and/or wrapping.

This method allows a user to examine a section of pipeline in which there may or may not be a fault and, by measuring attenuation along a chosen length of pipeline and comparing it with an expected attenuation along that length of pipeline, determine whether the section contains a fault. Alternatively, a plurality of measurements of attenuation along a chosen length of pipeline may be taken over time and changes in the measured attenuation monitored.

In a method according to the second aspect of this invention the difference in measured signal strength between a pair of adjacent spaced locations along the length of the pipeline in the direction of signal transmission may be a measure of the attenuation of the signal over that length of pipeline. The measurement of the signals applied to the pipeline from the plurality of spaced locations may generate a plurality of measured signal strengths and the method may comprise the step of calculating a plurality of attenuations for each of the plurality of lengths of pipeline located between respective pairs of spaced locations. The method may further comprise the step of averaging the calculated attenuations for each length of pipeline.

In this method because a signal is applied to the pipeline from several different locations, the attenuation along a particular length of pipeline may be measured several times. By taking an average of the measured attenuations along a length of pipeline, a more accurate measurement of attenuation may be obtained and more reliable identification of faults along that length of pipeline made.

The attenuation may be calculated in units which are independent of the applied signal strength. This makes comparison and averaging of different measured attenuations easier.

The measured attenuation across each length of pipeline may be expressed as a ratio of a predetermined expected attenuation to provide a plurality of attenuation ratios associated with each length of pipeline. These attenuation ratios may be multiplied together to produce an attenuation product for each length of pipeline. The method may further comprise the step of comparing calculated attenuation products to identify deterioration in each length of the pipeline. This has the effect of greatly increasing the resolution of the method so that it is much easier to identify a length of pipeline in which a fault is present.

In a method according to either the first or second aspects of the present invention the distance between each pair of adjacent spaced locations may be between 10 m and 100 m. The frequency of the signal applied to the pipeline may be between 5 kHz and 35 kHz and preferably between 10 kHz and 32 kHz.

According to a third aspect of the present invention there is provided a pipeline survey apparatus for use in a method according to the first or second aspects of the present invention, the apparatus comprising a plurality of sensor units, each sensor unit being spaceable from each other sensor unit above and along a length of the pipeline at a respective one of a plurality of spaced locations, at least one sensor unit comprising a non-contact coupling means for applying a signal to a pipeline and at least two sensor units each comprising a receiver for measuring signals emitted by a pipeline.

Preferably, each sensor unit comprises non-contact coupling means for applying a signal to a pipeline and receiver means for measuring signals emitted by a pipeline.

The non-contact coupling means may be an electromagnetic signal transmitter.

The apparatus may comprise a control unit, which control unit is arranged to receive data from each sensor unit and to perform calculations as referred to with respect to the second aspect of the present invention in order to measure deterioration in a pipeline.

The apparatus may comprise a sensor unit which is a master sensor unit, the master sensor unit comprising the control unit and further comprising a long range communication device. The long range communication device may be a GSM radio device.

Each sensor unit may comprise a short range radio system for communication with at least one other sensor unit.

The non-contact coupling means may be arranged to transmit a signal of between 5 kHz and 35 kHz and preferably to transmit a signal between 10 kHz and 32 kHz.

According to a fourth aspect of the present invention there is provided a pipeline survey system comprising a pipeline survey apparatus according to the third aspect of the present invention and a buried pipeline, which pipeline comprises a tubular member with a protective wrapping, wherein each sensor unit is spaced from each other sensor unit above and along the length of pipeline at a respective one of a plurality of spaced locations.

The sensor units may be regularly spaced along the pipeline with a spacing of between 10 and 100 m.

Each sensor unit, which is provided at a respective location, may be calibrated to take into account the distance between the sensor unit and pipeline at that respective location. Each receiver may have a sensor axis and each receiver may be arranged with its sensor axis orthogonal to the axis of the length of pipeline that passes under the respective location of that receiver. A sensor axis is a characteristic of the receiver which determines the strength of the signal detected.

The pipeline may comprise a cathodic protection system and each sensor unit may be arranged to monitor the voltage of the cathodic protection system.

Each sensor unit may be powered by a power unit, the power unit comprising a battery and a solar panel.

Throughout the specification the word "comprise", or variations such as "comprises" or "comprising", will be understood to imply the inclusion of the stated element, integer or step, or group of elements, integers or steps, but not the exclusion of any other element, integer or step, or group of elements, integers or steps.

A method of surveying a pipeline and a pipeline survey apparatus which embody this invention are described now, by way of example only, with reference to the accompanying drawings.

BRIEF SUMMARY OF THE INVENTION

A method of surveying a pipeline is provided. The pipeline comprises a tubular member with a protective wrapping. The method comprises the steps of applying signal to the pipeline from a first location, which first location is remote from the pipeline, and measuring the signal from a second and third locations. The second and third locations are remote from the pipeline and the second location is spaced from the third location along the pipeline. The signals received at the second and third location are used to provide an indication of deterioration of the signal along the tubular member and/or wrapping between the second and third locations.

One object of the present invention is to provide an improved method of surveying a pipeline.

Related objects and advantages of the present invention will be apparent from the following description.

BRIEF DESCRIPTION OF THE SEVERAL VIEWS OF THE DRAWINGS

FIG. 2c is a graph showing variation in pipeline current against distance from a signal source for a 27 kHz applied AC current;

FIG. 3 is a diagram showing schematically the layout of seven sensors along a length of pipeline;

FIG. 4 is a Table showing the emission and measurement sequence of the apparatus shown in FIG. 3;

DETAILED DESCRIPTION OF THE INVENTION

Figure 1:
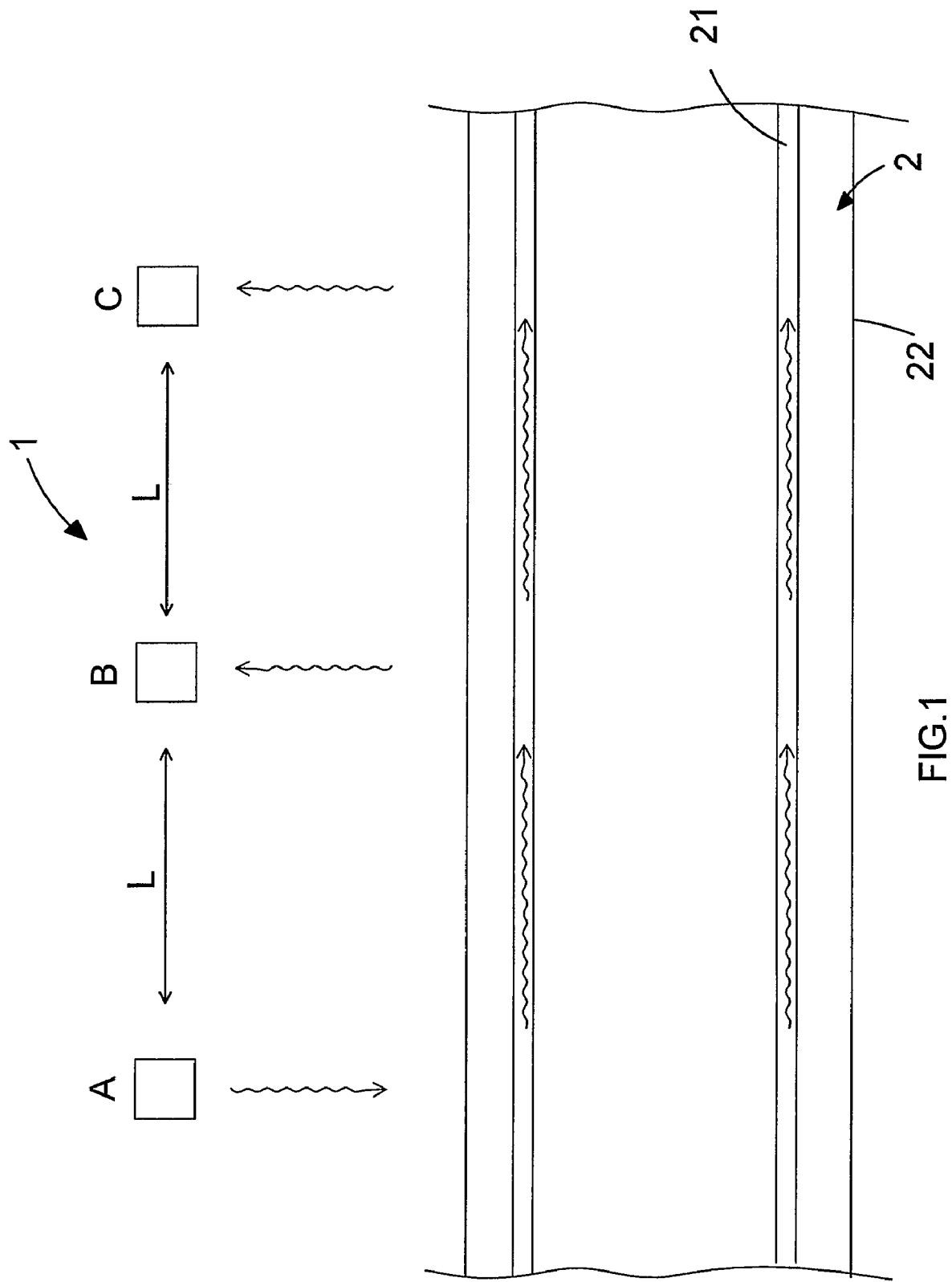
FIG. 1 is a schematic diagram of part of an apparatus for surveying a pipeline.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

FIG. 1 shows part of an apparatus 1 for monitoring a pipeline 2, which passes beneath the apparatus 1.

The pipeline 2 comprises a tubular member in the form of a pipe 21 and wrapping 22. The pipe 21 may have a diameter of between 7.6 cm (3 inches) and 142 cm (56 inches) or perhaps larger. The pipe 21 is made of steel. The wrapping 22 is provided to protect the pipe 21 from damage. The wrapping 22 may be a wrap or coating for the pipe 21. The wrapping 22 shown in FIG. 1 is a protective tape, made of plastics material, wrapped around the pipe 21. Good quality wrapping has a conductance of around $10^{18}$ $\Omega m^{-2}$.

The apparatus 1 comprises three sensor units A, B and C, spaced along the pipeline 2 by a common spacing L. In the apparatus 1 shown in FIG. 1, L is 50 m. The spacing between sensor units may be selected in accordance with the nature of the pipeline 2 to be monitored, but should preferably not be reduced below 15 m Each sensor unit A, B and C has a transmitter for transmitting an electromagnetic signal to the pipeline 2 and a receiver for detecting electromagnetic signals from the pipeline 2. In the embodiment shown in FIG. 1 the transmitter and receiver are provided as a combined sensor.

FIG. 1 illustrates the apparatus being used to monitor the section of pipeline 2 between sensor unit B and sensor unit C. In order to measure the deterioration of the length of pipeline between sensor units B and C the sensor at sensor unit A emits an electromagnetic signal. The emitted signal induces an AC current in the pipeline 2. This current passes away from sensor A in both directions along the pipeline 2. As the current passes along the pipeline 2 it attenuates. This attenuation is caused by emission of electromagnetic signals by the pipeline 2 back into the soil. Shortly after the transmission of electromagnetic signal by the sensor in sensor unit A a signal is measured by the sensor in sensor unit B and a signal is measured by the sensor in sensor unit C.

The strength of the signal emitted by the pipeline 2 into the soil in a particular region is dependent on the AC current in the pipeline 2 in that region. Accordingly, the signal received by the sensor in sensor unit B is stronger than the signal received by the sensor in sensor unit C. The difference in signal strengths received at sensor units B and C is indicative of AC current attenuation in the section of pipe 21 between sensor unit B and sensor unit C.

As will be described in more detail in due course the rate of current attenuation in a length of pipeline 2 is indicative of deterioration of the pipe 21 and/or wrapping 22. By comparing the signals received at sensor unit B and at sensor unit C a comparison of current attenuation along the length of pipeline 2 between sensor units B and C with an expected attenuation can be made. By use of this principle, the apparatus 1 is able to monitor deterioration of wrapping 22 and pipe 21.

In order to induce an AC current signal in a length of pipeline 2, it is important to select an appropriate frequency of electromagnetic signal to transmit from the sensor in sensor unit A. In general, a stronger signal may be induced in the pipeline 2 if a higher frequency electromagnetic signal is selected. However, the higher the frequency of the electromagnetic signal emitted, the higher the frequency of the AC current induced in the pipeline 2. However, high frequency AC currents attenuate more rapidly than lower frequency AC currents along a length of pipeline.

Figure 2A:
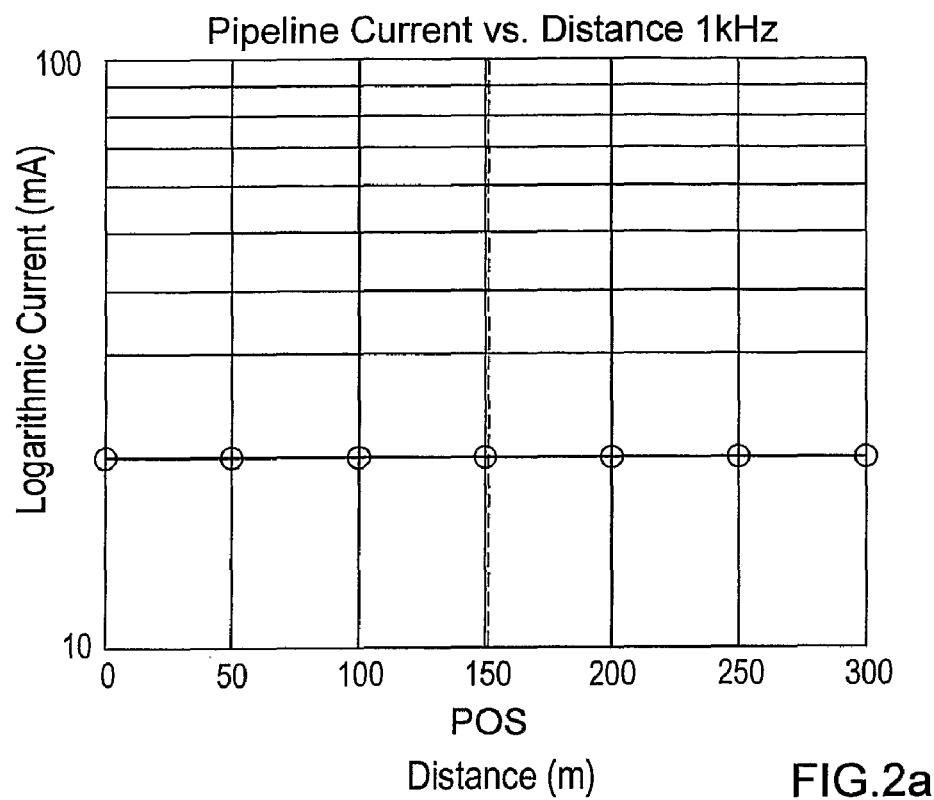
FIG. 2a is a graph showing variation in pipeline current against distance from a signal source for a 1 kHz applied AC current.
Figure 2B:
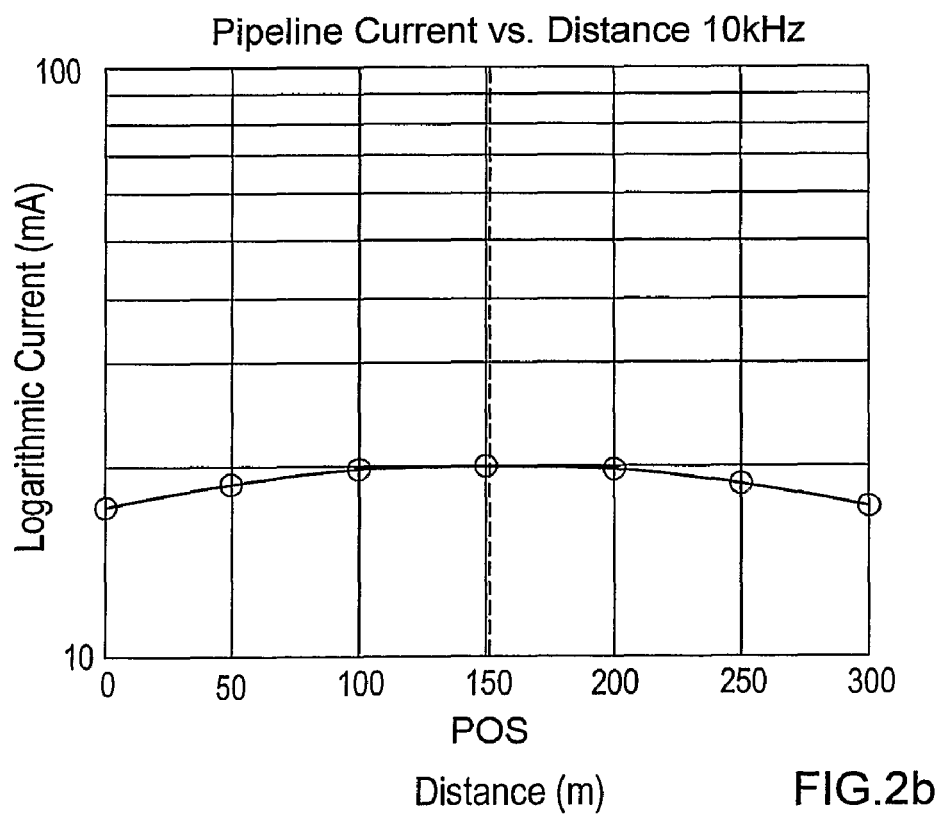
FIG. 2b is a graph showing variation in pipeline current against distance from a signal source for a 10 kHz applied AC current.

FIGS. 2a to 2c illustrate how current induced in the pipeline 2 attenuates with distance from the current source for different frequencies of induced AC current. Each graph shows distance linearly along the horizontal axis and current on a logarithmic scale on the vertical axis. In each case the current source is indicated by dotted line POS. The current source is located 150 m along the pipeline 2.

FIG. 2a shows pipeline current attenuation for a 1 kHz induced AC current. As can be seen from the figure, attenuation at this frequency is slow and the graph is approximately linear indicating logarithmic current attenuation away from the source.

FIG. 2b shows current attenuation along a pipeline for a 10 kHz induced AC current. As can be seen from this figure the current in the pipeline 2 starts to decrease more rapidly than logarithmically as distance from the current source increases. Current attenuation in the pipeline for a 10 kHz AC signal is quicker than that for a 1 kHz AC signal.

This effect is illustrated more dramatically in FIG. 2c which shows current attenuation for a 27 kHz induced AC current. As can be seen from this figure, a 20 ma current induced by a source is reduced to around 2 ma at a distance 150 m from the source.

There is a trade off when selecting a frequency to be emitted by the sensor unit transmitters. It is desirable to select a frequency that is high enough for good induction but a low enough to allow the AC current to travel a sufficient distance along the pipeline 2. A preferred frequency for use in this apparatus is in the range of 10 kHz to 32 kHz.

FIG. 3 shows the full length of the apparatus 1 for monitoring the pipeline 2, part of which was shown and described with reference to FIG. 1. The apparatus 1 has seven sensor units A to G provided at 50 m intervals along the pipeline 2.

The apparatus 1 operates in the following manner. Firstly the sensor in the sensor unit A transmits a signal which induces an AC current on the pipeline 2. Shortly thereafter, a signal is measured by the sensor at each of the sensor units B, C, D, E, F and G. When these measurements have been taken, the sensor in sensor unit B emits an electromagnetic signal inducing an AC current in the pipeline 2 and shortly thereafter a signal is sensed by the sensor in each of sensor units A, C, D, E, F and G. This process is repeated similarly until each of the sensor units A to G has emitted a signal which has been detected at each of the other sensor units.

FIG. 4 is a Table illustrating the measurements that may be made using this method. In the left hand column of FIG. 4, the sensor unit from which the electromagnetic signal is transmitted is indicated.

In the middle column of FIG. 4 is provided details of any blank sections. A blank section is a section of the pipeline for which no attenuation may be calculated. If, for example, a signal is emitted from the sensor in sensor unit C, no measurement of signal radiated by the pipeline may be made by sensor unit C. A measure of the signal at both ends of a section of pipeline is required in order to calculate the attenuation over that section of pipeline. Therefore, no current attenuation may be calculated for the sections of pipeline between sensor unit B and sensor unit C or between sensor unit C and sensor unit D.

The right hand column in FIG. 4 indicates those sections of the pipeline for which attenuation may be calculated. As may be seen from FIG. 4, if AC current can reach along the full length of the pipeline 2 then the attenuation of the current along each section of the pipeline 2 between adjacent sensor units may be measured five times. This repeated measurement of attenuation allows an accurate average attenuation for each section of pipeline to be calculated.

If the current attenuates so that readings may not be taken along the whole length of the pipeline 2, then fewer readings will be taken. However, if this system is to work at all (ie. the current passes far enough along the pipe for two readings to be taken and an attenuation calculated) then a section of pipe 21, which is not disposed at the end of the pipeline 2, will be measured at least twice.

Figure 5:
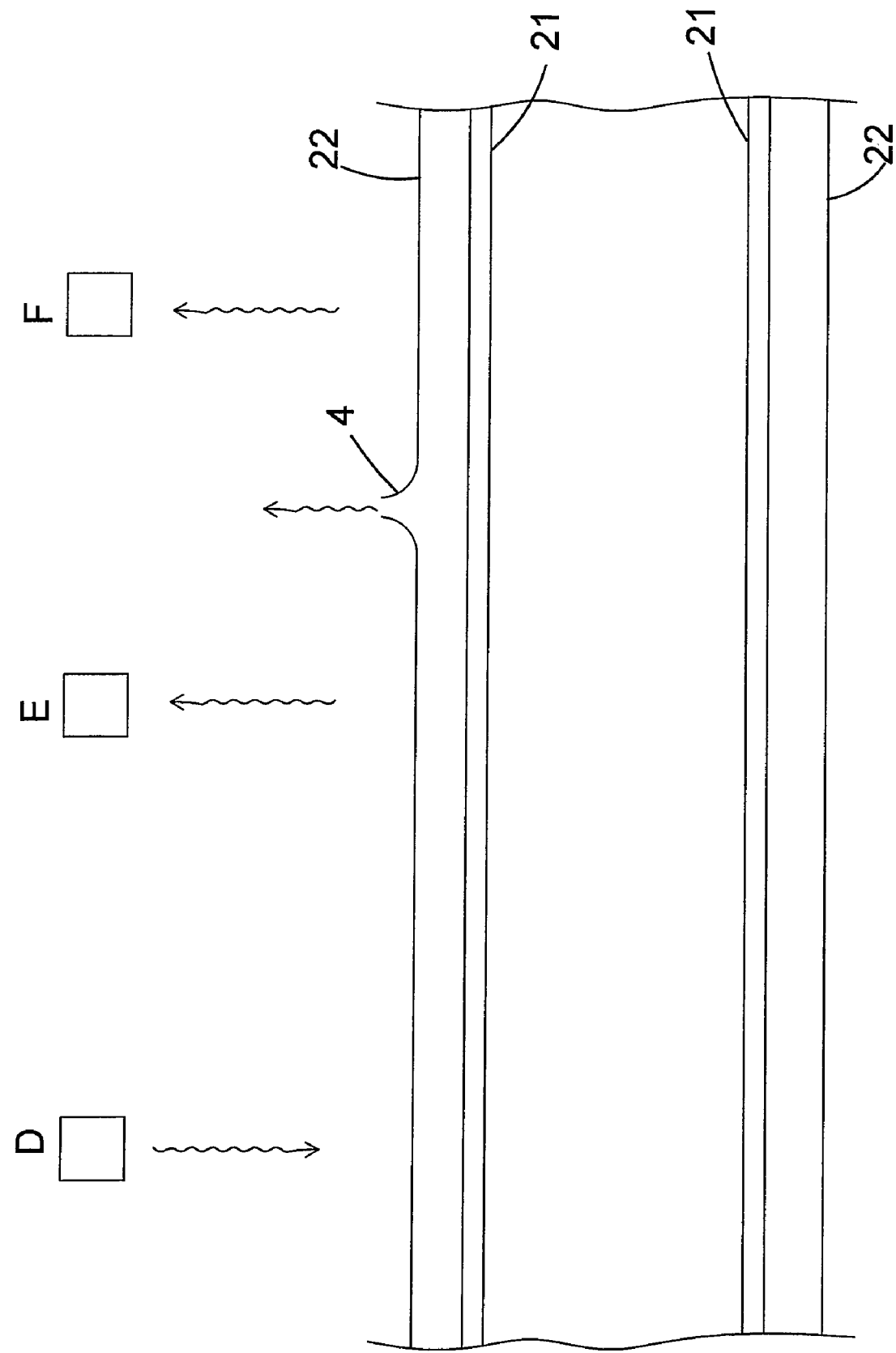
FIG. 5 shows part of the apparatus shown in FIG. 3 when there is a fault in the pipeline between two sensor units.

FIG. 5 is a schematic diagram showing the part of the apparatus shown in FIG. 3 between sensor unit D and sensor unit F. Common features, previously described with reference to FIG. 3, are indicated with corresponding numerals.

FIG. 5 shows the situation where a fault 4 is present in the pipeline wrapping 22 between sensor unit E and sensor unit F. The fault 4 introduces a low resistance electrical path from the pipe 21 to the soil. In this case, the fault 4 is a 1 meter section of pipe 21 with a wrapping conductance of 1000 µS/m². Consequently there is a substantial increase in the loss of AC current in the section of pipeline 2 between sensor unit E and sensor unit F. The fault 4 could be caused by incorrectly applied wrapping, mechanical damage to the wrap 21 before or during or after installation, decay of the wrap 21 due to soil conditions, disbonding of the wrap 21 from the pipe 22 allowing ground water to penetrate through the pipe 21 and providing an electrical path to earth or a leak in the pipe 21 itself causing the wrap 22 to fail at the leak point.

Figure 6:
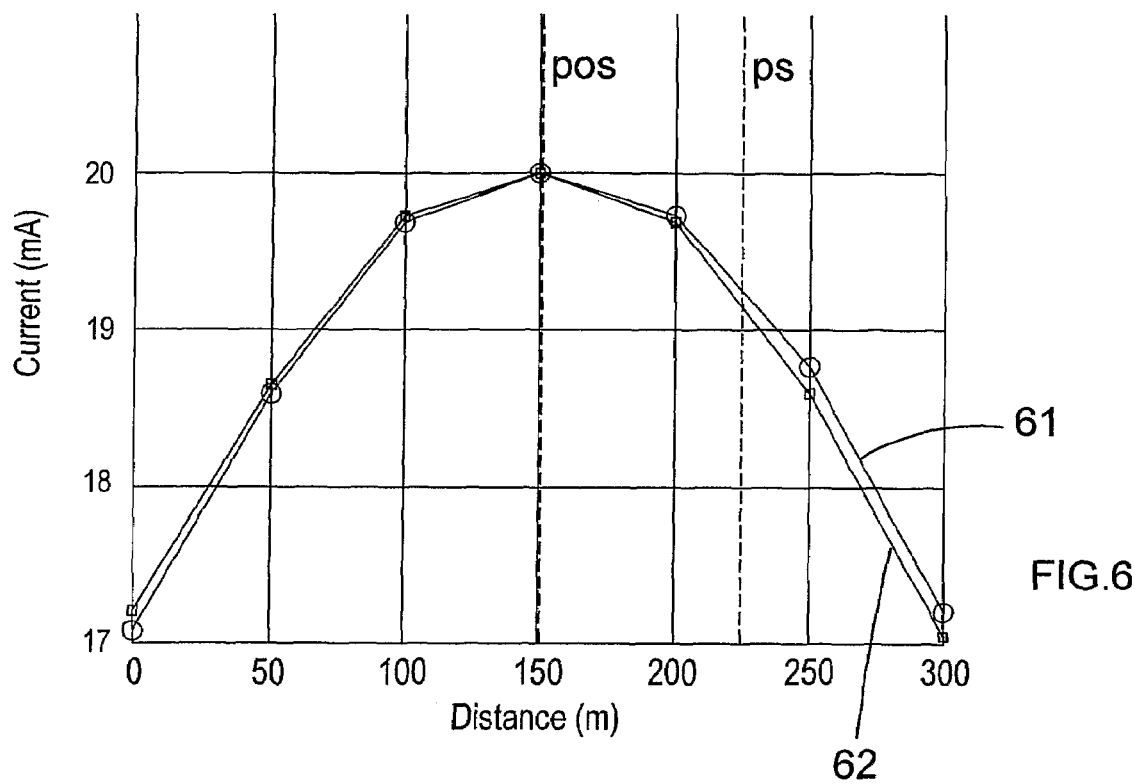
FIG. 6 is a graph showing pipeline current against distance from a signal source illustrating the effect of a fault in the pipeline on current attenuation in the apparatus shown in FIG. 5.

FIG. 6 is a graph showing pipeline current against distance for a 10 kHz AC current induced in the pipeline 2. The distance along the pipeline 2 and the location of sensor units A to G is indicated on the horizontal axis and the current in the pipeline in milli amps is provided on the vertical axis. Current is induced in the pipeline 2 by the sensor at sensor unit D located 150 m along the pipeline 2.

The graphs shows two plots. The first plot 61 indicates the current against distance characteristics for a length of pipeline 2 in which no faults are present. The second plot 62 indicates the current against distance characteristics of the pipeline 2 shown in FIG. 5 in which there is a fault between the sensor unit E and sensor unit F, around 225 m along the length of the pipe.

The presence of a fault between sensor unit E and sensor unit F results in increased attenuation between sensor unit E and sensor unit F. The signals measured at sensor units F and G indicate a lower current flowing in the pipeline 2 than would be the case if the pipeline 2 contained no faults. However, at this stage it should be noted that it is relatively difficult to identify the section of pipeline 2 in which there is a fault from this Figure.

Figure 7:
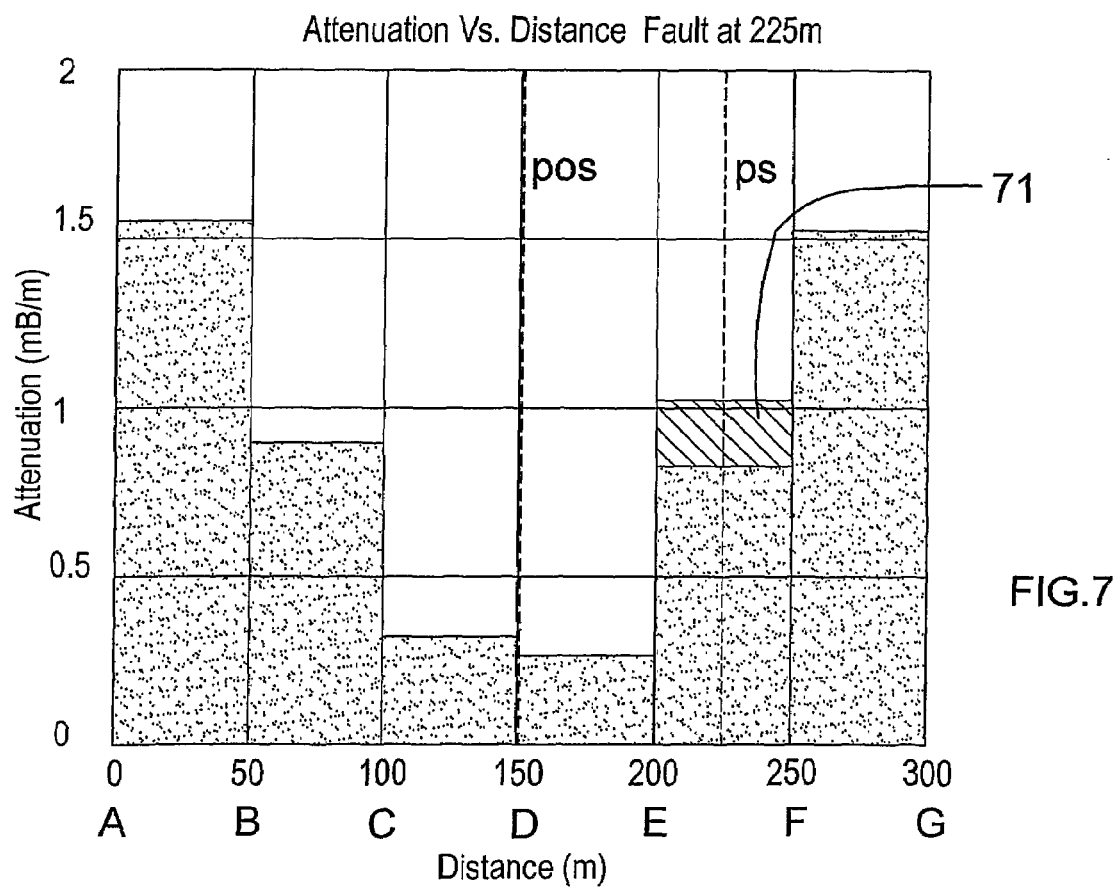
FIG. 7 is a graph showing attenuation against distance for the apparatus shown in FIG. 5.

FIG. 7 is a graph showing attenuation against distance. The distance along the pipeline is shown on the horizontal axis. Attenuation is indicated on the vertical axis in units if milli bells per metre. The attenuation is calculated as 2,000×log $I_1/I_2$ where $I_1$ is the current measured at the start of the section of pipeline 2 and $I_2$ is the current measured at the end of the section of pipeline 2. The hatched area 71 in FIG. 7 indicates the difference in attenuation in the section of pipeline 2 between sensor E and sensor F caused by the fault 4 in that section. Again it is difficult to see from this graph which section of pipe has a fault or even if a fault is present.

Figure 8:
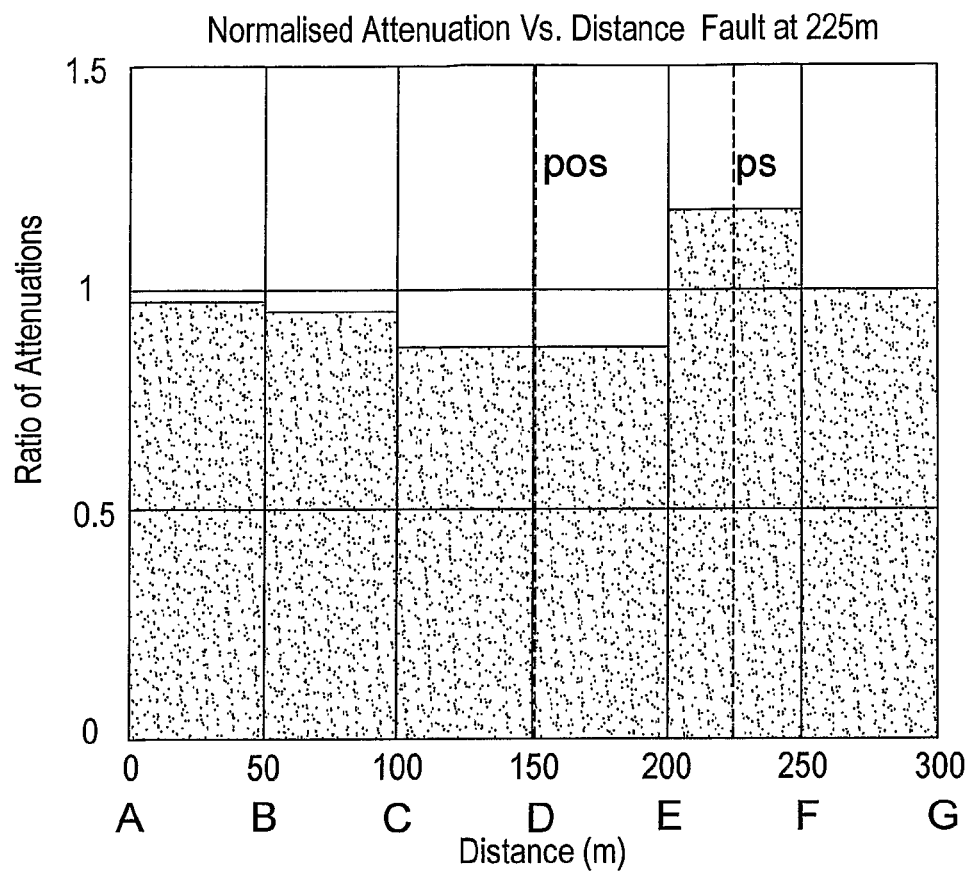
FIG. 8 is a graph showing normalised attenuation versus distance for the apparatus illustrated in FIG. 5.

FIG. 8 is a graph showing normalised attenuation (also referred to as ratio of attenuation) against distance. The normalised attenuation is the attenuation, as shown in the graph of FIG. 7, divided by the expected attenuation for a fault-free section of pipe. As can be seen from FIG. 8, the ratio of attenuation for most sections of pipe located between adjacent sensor units is around 1 indicating that the attenuation in those sections of pipeline is similar to that expected for fault-free pipe. However, the exception to this is the section of pipeline 2 between sensor unit E and sensor unit F, in which there is a fault 4. It is much easier to spot the deviation from expected attenuation in this graph. Therefore, by calculating the normalised attenuation it is possible to readily identify the existence of a fault 4 in the section of pipeline 2 and to identify between which two sensor units the fault 4 is located.

The expected attenuation for a fault-free length section of pipeline 2 may be the level of attenuation in the pipeline 2 when the pipeline 2 was last inspected. At that time the pipeline 2 should have been brought up to at least a minimum level of integrity by repair of the wrapping 22.

As mentioned with reference to FIGS. 3 and 4 by sequentially causing sensor units A to G to induce an AC current in the pipeline 2, multiple measurements of the attenuation across each section of pipeline between adjacent pairs of sensor units may be taken. For each of these sets of measurements the ratio of attenuation may be calculated. If these ratios of attenuation are multiplied together, a graph of product of ratio of attenuations against distance along the pipeline may be produced. Such a graph is shown in FIG. 9.

Figure 9:
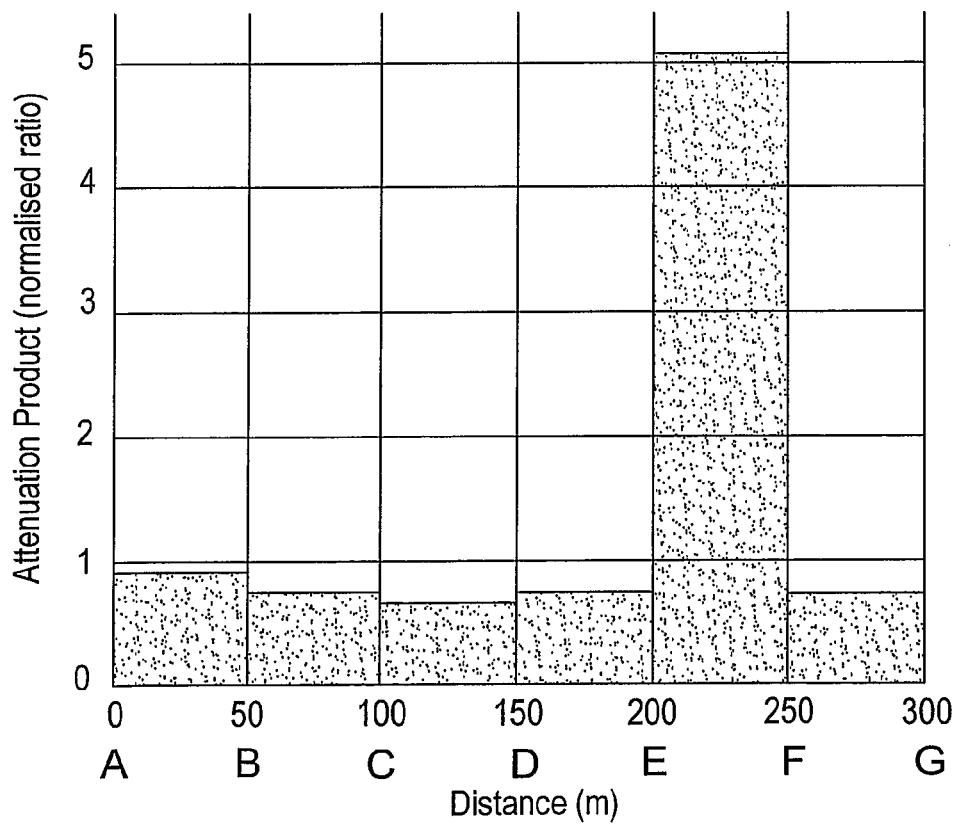
FIG. 9 is a graph showing the product of the ratio of attenuations against distance for the apparatus illustrated in FIG. 5.

As can be seen from FIG. 9, multiplying together the attenuation ratios for each of the five measurements greatly increases the resolution. The presence of a fault 4 in the pipeline section between the sensor E and sensor unit F is now very clear. Accordingly, by calculating a product of ratio attenuations and looking for significant deviations away from 1 it is possible to identify sections of pipeline 2 between pairs of sensor units that contain faults 4.

Figure 10:
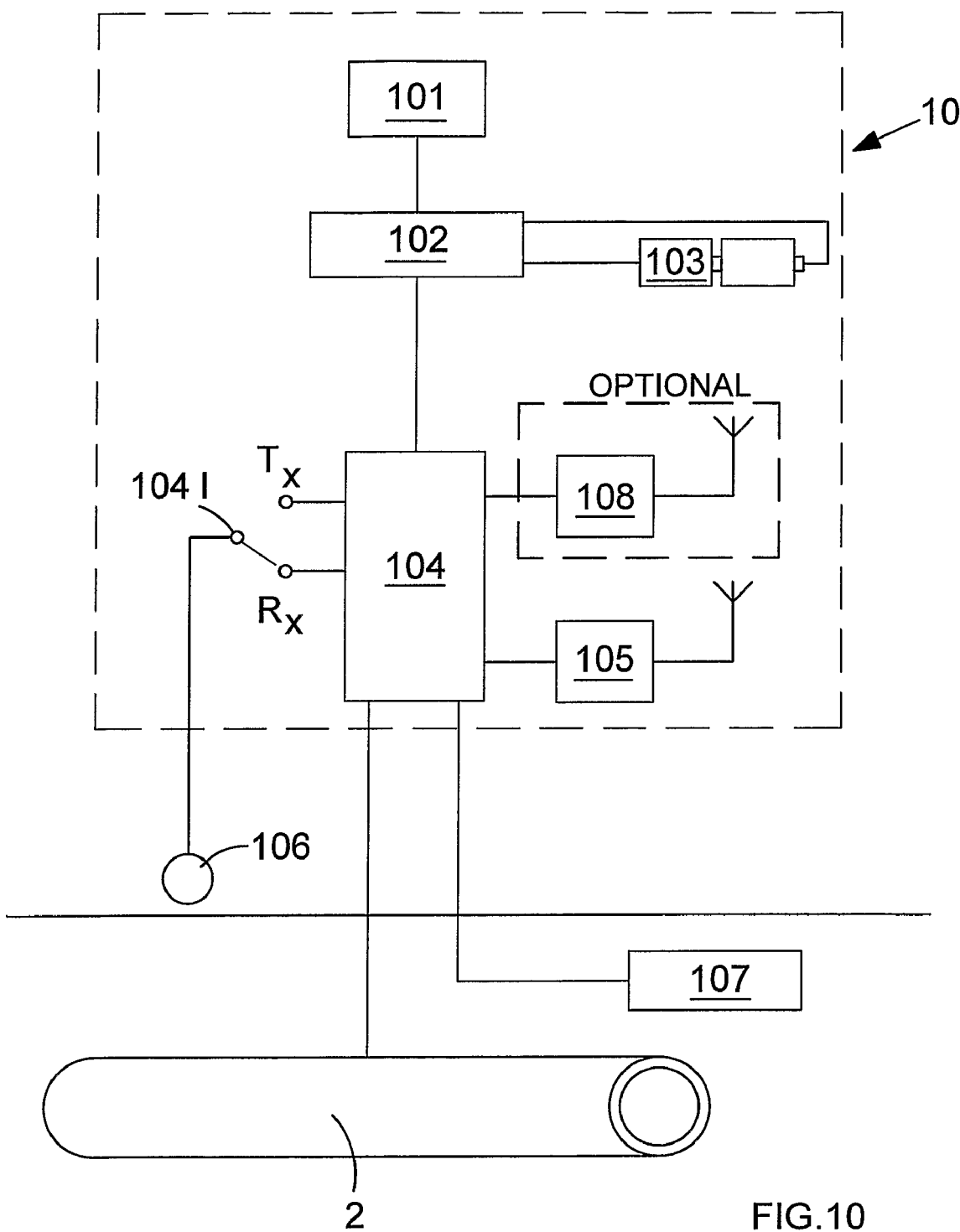
FIG. 10 shows the structure of a sensor unit.

FIG. 10 illustrates in more detail the structure of a sensor unit 10. The sensor unit comprises a solar panel 101, a power management unit 102 connected to a battery pack 103, a processor 104 and a short range radio unit 105. The processor 104 is arranged to control operation of the sensor unit 10.

The solar panel 101, the power and management unit 102 and the battery pack 103 serve to provide a long life and low maintenance power supply for the sensor unit 10. The solar panel 101 should be arranged at an angle on the sensor unit 10 according to the latitude at which the sensor unit is located and be arranged to face north or south, as appropriate, for efficient power generation.

The sensor unit 10 is connected to a sensor 106, which as previously mentioned, acts as both a transmitter and a receiver. The sensor 106 is controlled by the processor 104. When the sensor 106 is connected to an Rx input to the processor 104 (as shown in FIG. 10) the sensor 106 operates as a receiver. In this mode, the sensor 106, which comprises a coil, outputs a voltage, which is proportional to the current flowing in the pipeline 2 and the distance of the sensor 106 from the pipeline 2. When the sensor 106 is connected to a Tx input of the processor 104, the sensor 106 operates as transmitter.

Figure 11:
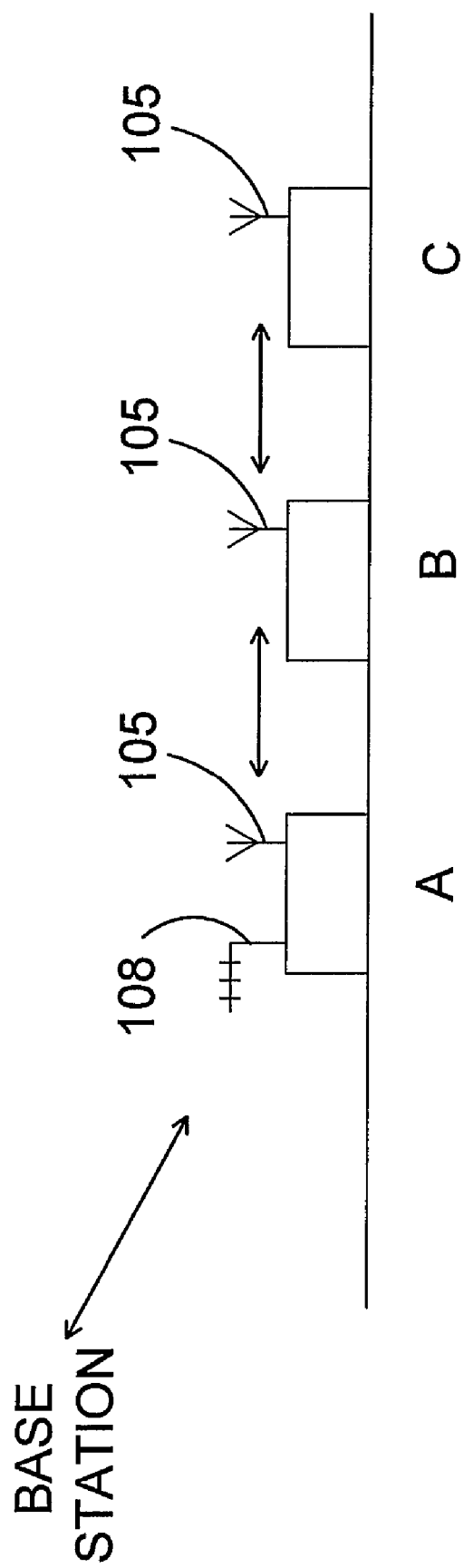
FIG. 11 shows part of the apparatus of FIG. 3 illustrating communication between sensor units and between the apparatus and a base station.

Control of the operation of the apparatus 1 will be described with reference to FIG. 11 which shows sensor units A, B and C. However, operation of sensor units D to G is similar. The sensor units are provided in a row along the pipeline 2. The short range radio unit 105 at each sensor unit A, B, C is strong enough to transmit a signal over the full length of the pipeline 2, allowing data to be transmitted between sensor units 10. However, in an alternative apparatus, the short range radio may only be strong enough to transmit over the 50 m between adjacent sensor units. Thus, data concerning electromagnetic signals received at the sensor 106 may be relayed up and down the chain of sensor units A to G as required.

The frequency of the short range radio link should be selected to avoid signals from other sources interfering with operation of the apparatus 1. The apparatus 1 may comprise a system for monitoring foreign signals (not shown), which is arranged to raise an alarm if the signals persist for longer than a predetermined time.

Sensor unit A is designated a master sensor unit. As the master sensor unit, sensor unit A comprises a long range radio device 108 which is illustrated in a box marked as optional in FIG. 10. This long range radio device 108 is a GSM radio device.

The master sensing unit A controls the sequencing of the apparatus 1. Once each sensor unit 10 has been sequentially operated to induce current in the pipeline 2 and appropriate readings from the other sensors 106 have been taken, the sensor unit A interrogates the other sensor units 10 to obtain the results of measurements taken. Once this data is received from each of the sensor units, sensor unit A perform calculations as described with reference to FIGS. 6 to 9 and determines the change in current attenuation from previous surveys.

The apparatus 1 calculates the current induced in the pipeline 2 based on signals received in a particular frequency range. The apparatus 1 takes no account of signals received outside of this frequency range. The apparatus, therefore, is not adversely affected by AC current induced in the pipeline 2 by, for example, power transmission lines. The apparatus 1 may be provided with a monitoring system to monitor other AC currents in the pipeline 2.

The apparatus 1 monitors the pipeline 2 for breach of certain predetermined limits. These predetermined limits may be, amongst other things, a high rate change of measured attenuation, a measured attenuation above an upper limit or a discontinuity in the measured attenuation.

A high rate of change of measured attenuation in a section of pipeline 2 suggests that the pipeline 2 may have been exposed for some reason (possibly by a third party) or that a leak is present.

Measured attenuation above a predetermined limit suggest that the pipeline 2 should be investigated. As the pipeline wrapping 22 degrades over time, the rate of attenuation gradually increases. Breach of a predetermined level of measured attenuation may trigger a review of the pipeline's cathodic protection system. The master sensor unit 10 allows a new predetermined level of attenuation to be input, which may be done after a review of the pipeline 2 to more closely reflect the wrapping condition then present in the pipeline 2.

An apparent discontinuity in the measured attenuation in a section of pipeline 2 may represent a catastrophic failure.

If the pipeline 2 causes attenuation outside a predetermined limit then the master sensor unit A transmits this information to a base station. This communication link is sent via long range radio link 108. The base station may be the mobile phone of a pipeline operator and the communication from the master sensing unit A may be a text message.

The processor 104 in the master sensor unit A may be programmed to control the master sensor unit to perform a survey of the pipeline in hourly intervals. Alternatively, the master sensor unit A may be programmed to operate "on demand" so that a survey of the pipeline 2 is performed upon receipt of a predetermined signal via the long range radio link 108. Preferably the time taken for a survey, for a system comprising 7 sensor units, should not exceed 1 minute.

The apparatus 1 is capable of preforming a self test for correct functioning. This check may be initiated on demand from the base station by sending a signal via the long range radio link 108. The test for correct function may involve use of a switchable anomaly in the pipe. The switchable anomaly may be controlled to introduce an artificial fault in to the pipe for testing purposes. The artificial anomaly should then be removable from the pipeline 2 to allow normal operation. Further, the apparatus 1 may be arranged to send a signal to the base station 1 in the event of a partial or complete apparatus failure.

The preferred arrangement of the sensor units 10 is with each sensor unit 10 at the same distance from the pipeline 2. However, this may not be possible, for example due to local geography. The lateral offset and depth of the pipeline 2 from the sensor unit 10 may be input and permanently stored in the sensor unit 10. These values may then be used in calculating the current in the pipeline 2 based on signals received at the sensor 106. The sensor units 10 should be calibrated to give the same reading for a given current passing through the pipeline 2 in the sensor unit's vicinity.

In sensor units of the type shown in FIG. 10 the sensor unit may also be arranged to read the voltage of the cathodic protection system of the pipeline 2 on demand. In order to read the cathodic protection voltage the sensor unit 10 needs to be connected to the pipeline 2 via a cathodic protection test post. It is further necessary to provide remote earth 107 to act as a reference voltage. The sensor unit 10 may also comprise a tamper system which would issue an alert to the base station in the event that the sensor unit is interfered with.

Whilst the apparatus 1 described above is made up of 7 sensor units 10, there is in principle no limit on the number of sensor units that may be provided. If a long section of pipeline is to be monitored, it may be desirable to provide more than one master sensor unit for performing calculations and to communicate with one or more base stations.

As suggested in the introduction, the present invention may find use in monitoring high consequence areas. In such applications, it is preferable for sensor units to be provided along the pipeline passing through the high consequence area and also in a portion of the pipeline extending on both sides of the high consequence area. For short sections of pipeline passing through high consequence areas it may be sufficient to just provide a sensor unit on both sides of the high consequence area and to monitor the high consequence area as a single section. If the high consequence area is larger it may be necessary to provide one or more sensor units within the high consequence area.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A method of surveying a buried pipeline, which pipeline comprises a tubular member with a protective wrapping, comprising the step of selecting a plurality of spaced locations above and along the length of the pipeline, and sequentially from each spaced location applying a signal to the pipeline and measuring the signal at each of the other spaced locations, wherein the difference in measured signal strength between a pair of adjacent spaced locations along a length of the pipeline in the direction of signal transmission is a measure of the attenuation of the signal over that length of pipeline and the measurement of the signals applied to the pipeline from the plurality of spaced locations generates a plurality of measured signal strengths, the method comprising the step of calculating a plurality of attenuations for each of the plurality of lengths of pipeline located between respective pairs of spaced locations and the method further comprising the step of averaging the calculated attenuations for each length of pipeline.

2. A method according to claim 1 wherein the attenuation is calculated in units which are independent of the applied signal strength.

3. A method according to claim 1 wherein each measured attenuation across each length of pipeline is expressed as a ratio of a predetermined expected attenuation to provide a plurality of attenuation ratios and the attenuation ratios associated with each length of pipeline are multiplied together to produce an attenuation product for each length of pipeline, the method further comprising the step of comparing the attenuation products to provide an indication of deterioration in each length of the pipeline.

4. A method according to claim 1 wherein the distance between each pair of adjacent spaced locations is between 10 and 100 meters.

5. A method according to claim 1 wherein the frequency of the signal applied to the pipeline is between 5 kHz and 35 kHz.

6. A method according to claim 1 wherein the frequency of the signal applied to the pipeline is between 10 kHz and 32 kHz.

7. A pipeline survey apparatus for use in a method according to claim 1, the apparatus comprising a plurality of sensor units, each sensor unit being spaceable from each other sensor unit above and along a length of the pipeline at a respective one of a plurality of spaced locations, at least one sensor unit comprising a non-contact coupling means for applying a signal to a pipeline and at least two sensor units each comprising a receiver for measuring signals emitted by a pipeline.

8. An apparatus according to claim 7 wherein each sensor unit comprises non-contact coupling means for applying a signal to a pipeline and a receiver for measuring signals emitted by a pipeline.

9. An apparatus according to claim 7 comprising a control unit, which control unit is arranged to receive data from each sensor unit and to perform calculations in order to measure deterioration in a pipeline.

10. An apparatus according to claim 9 wherein a sensor unit is a master sensor unit, the master sensor unit comprising the control unit and further comprising a long range communication device.

11. An apparatus according to claim 10 wherein the long range communication device is a GSM radio device.

12. An apparatus according to claim 7 wherein each sensor unit comprises a short range radio device for communication with at least one other sensor unit.

13. An apparatus according to claim 7 wherein the non-contact coupling means is arranged to transmit a signal of between 5 kHz and 35 kHz.

14. An apparatus according to claim 7 wherein the non-contact coupling means is arranged to transmit a signal of between 10 kHz and 32 kHz.

15. An apparatus according to claim 7 wherein each sensor unit is powered by a power unit, the power unit comprising a battery and a solar panel.

16. A pipeline survey system comprising a pipeline survey apparatus according to claim 7 and a buried pipeline, which pipeline comprises a tubular member with a protective wrapping, wherein each sensor unit is spaced from each other sensor unit above and along the length of pipeline at a respective one of a plurality of spaced locations.

17. An system according to claim 16 wherein the plurality of sensor units are regularly spaced along the pipeline with a spacing of between 10 and 100 meters.

18. An system according to claim 16 wherein each sensor unit, which is provided at a respective location, is calibrated to take into account the distance between the sensor unit and the pipeline at that respective location.

19. An apparatus according to claim 16 wherein each receiver has a sensor axis and each receiver is arranged with its sensor axis orthogonal to the axis of the length of pipeline that passes under the respective location of each receiver.

20. An apparatus according to claim 16 wherein the pipeline comprises a cathodic protection system and each sensor unit is arranged to monitor the voltage of the cathodic protection system.

21. A method according to claim 1 wherein the step of applying a signal to the pipeline comprises the step of inducing an electric current in the pipeline by electromagnetic induction.

* * * * *